United States Patent [19]

Adolph

[11] 4,453,021

[45] Jun. 5, 1984

[54] DINITROPROPYL FLUORODINITROETHYL FORMAL PLASTICIZER AND METHOD OF PREPARATION

[75] Inventor: Horst G. Adolph, Silver Spring, Md.

[73] Assignee: The United States of Americaas represented by the Secretary of the Navy, Washington, D.C.

[21] Appl. No.: 453,674

[22] Filed: Dec. 27, 1982

[51] Int. Cl.$^3$ .................. C07C 43/00; C07C 79/34
[52] U.S. Cl. ........................... 568/590; 149/88
[58] Field of Search .................. 149/88; 568/590

[56] References Cited

U.S. PATENT DOCUMENTS 3,705,197 12/1972 Kaplan et al. .................. 149/88 X
3,873,626 3/1975 Adolph .......................... 149/88 X

OTHER PUBLICATIONS

Fremenko et al., Chem. Abs., 87275t, pp. 383 to 384.

Primary Examiner—Leland A. Sebastian
Attorney, Agent, or Firm—Robert F. Beers; Kenneth E. Walden; Roger D. Johnson

[57] ABSTRACT

2,2-dinitropropyl 2-fluoro-2,2-dinitroethyl formal which is prepared by the following processes:

(1)

$$CH_3C(NO_2)_2CH_2OH + CF(NO_2)_2CH_2OH + CH_2O \xrightarrow[H_2SO_4]{75-80\%}$$

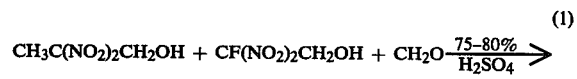

$$CH_3C(NO_2)_2CH_2OCH_2OCH_2CF(NO_2)_2$$

or $$CH_3C(NO_2)_2CH_2OH + CH_2O \xrightarrow{AlCl_3} \quad (2)$$

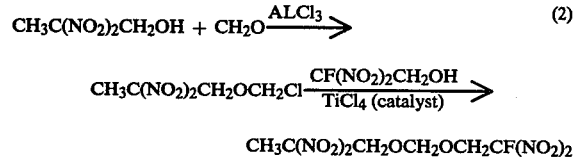

$$CH_3C(NO_2)_2CH_2OCH_2Cl \xrightarrow[TiCl_4 \text{ (catalyst)}]{CF(NO_2)_2CH_2OH}$$

$$CH_3C(NO_2)_2CH_2OCH_2OCH_2CF(NO_2)_2$$

6 Claims, No Drawings

DINITROPROPYL FLUORODINITROETHYL FORMAL PLASTICIZER AND METHOD OF PREPARATION

BACKGROUND OF THE INVENTION

This invention relates to organic formals and more particularly to polynitro organic formals.

Bis(2-fluoro-2,2-dinitroethyl) formal (FEFO) and Bis(2,2-dinitropropyl) formal (BDNPF) are used as energetic plasticizers in explosive and propellant compositions. FEFO has a high energy content but is volatile and toxic and has a relatively high melting point. BDNPF is low in energy and has an even higher melting point, requiring the use of an energy-decreasing melting point depressant. Mixtures of FEFO and BDNPF can be used to obtain a lower melting point and intermediate levels of energy and volatility, but the improvements in melting point and volatility are small at the eutectic composition of approximately 70% FEFO and 30% BDNPF.

SUMMARY OF THE INVENTION

Accordingly, an object of this invention is to provide a new organic compound.

Another object of this invention is to provide an improved energetic plasticizer having a low melting point and low vapor presssure.

A further object of this invention is to provide an improved energetic plasticizer having a high oxygen content.

Yet another object of this invention is to provide an improved energetic plasticizer which has good thermal stability.

A still further object of this invention is to provide a method of preparing a new organic compound.

These and other objects of the invention are accomplished by providing 2,2-dinitropropyl 2-fluoro-2,2-dinitroethyl formal. This formal is produced by reacting formaldehyde, 2,2-dinitropropanol, and aluminum chloride to produce chloromethyl 2,2-dinitropropyl ether. This ether is then reacted with 2-fluoro-2,2-dinitroethanol in the presence of titanium tetrachloride as a catalyst to produce the desired 2,2-dinitropropyl 2-fluoro-2,2-dinitroethyl formal. A second method of preparation is to react 2,2-dinitropropanol, 2-fluoro-2,2-dinitroethanol, and formaldehyde in 75% to 80% sulfuric acid to produce the 2,2-dinitropropyl 2-fluoro-2,2-dinitroethyl formal. In both processes the product 2,2-dinitropropyl 2-fluoro-2,2-dinitroethyl formal can be separated from the by-products of the reaction via preparative liquid chromatography.

2,2-dinitropropyl 2-fluoro-2,2-dinitroethyl formal is useful as an energetic plasticizer for propellants and explosives.

DETAILED DESCRIPTION OF THE PREFERRED EMBODIMENTS

The present invention provides a new compound 2,2-dinitropropyl 2-fluoro-2,2-dinitroethyl formal having the formula

$$CH_3C(NO_2)_2CH_2OCH_2OCH_2CF(NO_2)_2.$$

This unsymmetrical formal combines the 2,2-dinitropropyl and 2-fluoro-2,2-dinitroethyl moieties into the same molecule; thus, they can not be separated. In contrast, in the prior art, physical admixtures of bis(2,2-dinitropropyl) formal (BDNPF) and bis(2-fluoro-2,2-dinitroethyl) formal (FEFO) were used. However, FEFO is volatile and toxic while BDNPF is low in energy and tends to crystalize out. Thus FEFO and BDNPF tended to separate through evaporation, migration, or crystallization.

Two processes for preparing 2,2-dinitropropyl 2-fluoro-2,2-dinitroethyl formal are illustrated by examples 1 and 2 below. In the first process (example 1), 2,2-dinitropropanol, 2-fluoro-2,2-dinitroethanol, and formaldehyde (added as paraformaldehyde) are reacted in a 1:1:1 molar ratio in 75% to 80% sulfuric acid. The paraformaldehyde is first dissolved in the sulfuric acid. A equimolar mixture of the two alcohols is then added to the sulfuric acid reaction mixture. During this addition, the reaction mixture is kept at a temperature in the range of from above the freezing point of the mixture up to room temperature, but preferably in the range of from −5° C. to 5° C. This is done by stirring and external cooling. The mixture is allowed to react for several hours.

The product is then extracted out by conventional means as illustrate by example 1. The organic solvent used for extraction in example 1 was dichloromethane, but similar inert chlorohydrocarbon solvents such as 1,2-dichloroethane and 1,1,2-trichloroethane may also be used.

The product is a mixture of approximately 80 percent of the unsymmetrical 2,2-dinitropropyl 2-fluoro-2,2-dinitroethyl formal and 20 percent of the symmetrical bis(2,2-dinitropropyl) formal and bis(2-fluoro-2,2-dinitroethyl) formal. This mixture is useful as an energetic plasticizer with substantially less tendency to separate than a binary eutectic mixture of the symmetrical formals. However, if it is preferred to use pure unsymmetrical 2,2-dinitropropyl 2-fluoro-2,2-dinitroethyl formal, the pure unsymmetrical formal can be obtained by preparative liquid chromatography as illustrated in example 2.

In the second method of preparing unsymmetrical 2,2-dinitropropyl 2-fluoro-2,2-dinitroethyl formal (example 2) all the following reactions are carried out in an atmosphere of dry, inert gas (e.g., argon, neon, nitrogen). First, aluminum chloride is added to a solution of equal molar parts of formaldehyde (as trioxane) and 2,2-dinitropropanol which is agitated (e.g., stirred) and cooled to a temperature of about −5° C. to room temperature, but preferably from −5° C. to 5° C. Any suitable inert solvent, such as dichloromethane, 1,2-dichloroethane, or 1,1,2-trichloroethane may be used as the solvent. The reaction mixture is then kept at ambient (room) temperature until the product chloromethyl 2,2-dinitropropyl ether is formed. The product ether is then isolated by conventional means as illustrated in example 2.

Next, the chloromethyl 2,2-dinitropropyl ether is reacted with an equal molar amount of 2-fluoro-2,2-dinitroethanol in the presence of titanium tetrachloride as a catalyst. The reaction mixture is heated at from about 50° C. to about 90° C., but preferably from 80° C. to 90° C., until the product 2,2-dinitropropyl 2-fluoro-2,2-dinitroethyl formal is formed. Again the product is isolated by conventional means (e.g., see example 2). As in method 1, the product is a mixture of approximately 80 percent of the unsymmetrical 2,2-dinitropropyl 2-fluoro-2,2-dinitroethyl formal and 20 percent of the symmetrical bis(2,2-dinitropropyl) formal and bis(2- fluoro-2,2-dinitroethyl) formal. This mixture is in itself useful as an energetic plasticizer; if the pure 2,2-dinitropropyl 2-fluoro-2,2-dinitroethyl formal is preferred. It is isolated from the mixture by preparative liquid chromatography as illustrated by example 2.

To more clearly illustrate this invention, the following examples are presented. It should be understood, however, that these examples are presented merely as a means of illustration and are not intended to limit the scope of the invention in any way.

EXAMPLE 1

2-2-dinitropropyl 2-fluoro-2,2-dinitroethyl formal preparation in sulfuric acid

Three grams of paraformaldehyde was dissolved in 50 ml 80% sulfuric acid. With stirring and cooling (ice-bath), a mixture of 16 g 2,2,2-fluorodinitroethanol and 15.5 g 2,2-dinitropropanol was added rapidly, and the reaction mixture was stirred 20 hours at room temperature. The product was extracted into dichloromethane and the extracts were washed with one 100 ml and two 50 ml portions of 0.1 N NaOH, then with water, and were dried over $MgSO_4$. Removal of the solvent in vacuo gave 25 g (76%) of an oil which consisted by nuclear magnetic resonance (NMR) analysis of approximately 80% unsymmetrical and 20% symmetrical formals. The use of 75% sulfuric acid decreased the yield somewhat but did not strongly affect the product composition; however, the use of more concentrated sulfuric acid increased the FEFO content of the reaction product at the expense of unsymmetrical formal.

The product 2,2-dinitropropyl 2-fluoro-2,2-dinitroethyl formal was isolated by preparative liquid chromatography as described below in example 2.

EXAMPLE 2

2,2-dinitropropyl 2-fluoro-2,2-dinitroethyl formal from chloromethyl 2,2-dinitropropyl ether 8.8 grams of aluminum chloride was added rapidly to an ice-cooled solution of 9.9 g 2,2-dinitropropanol and 2.0 g trioxane in 50 ml dry dichloromethane under a nitrogen atmosphere. The mixture was stirred 2 days at room temperature, then it was poured onto crushed ice and the mixture stirred vigorously until all aluminum precipitates had dissolved (addition of some sulfuric acid may be required). The product solution was separated, the aqueous phase extracted with dichloromethane, and the extracts washed rapidly with a near saturated, ice cold sodium hydrogen carbonate solution. After drying ($MgSO_4$) the solvent was evaporated in vacuo to give 12.0 g (92%) crude chloromethyl dinitropropyl ether, purity 98% by gas-liquid phase chromatography (GLPC). $^1$H NMR ($CDCl_3$): $\delta 2.18$, s (3H); 4.49 (2, 2H); 5.44 (s,2H).

To a solution of 1.5 g 2-fluoro-2,2-dinitroethanol and 2.0 g crude chloromethyl 2,2-dinitropropyl ether in 10 ml dry ethylene dichloride under a nitrogen atmosphere was added ten drops titanium tetrachloride and the solution was heated at 90° C. for 18 hours. After cooling, the mixture was poured over crushed ice containing some sulfuric acid and stirred until the organic phase was clear. After separation the organic phase was washed with 0.1 N NaOH and with water, dried ($MgSO_4$) and stripped to give 2.5 g oil which by NMR and GPC analysis consisted of approximately 80% of the title compound and 20% of a mixture of symmetrical bis(2,2-dinitropropyl) formal and bis(2-fluoro-2,2-dinitroethyl) formal.

Pure 2,2-dinitropropyl 2-fluoro-2,2-dinitroethyl formal was obtained from this mixture or that of example 1 by preparative liquid chromatography. A solution of the formal mixture in dichloromethane/hexane (7:3) was chromatographed on silica gel with the same solvent and the progress of the separation monitored by NMR. Two or three passes through the column were required for complete separation. The pure title compound was obtained as a pale yellow oil which did not crystallize on extended storage. The density was found to be 1.50 g/cm$^3$.

Analysis. Calculated for $C_6H_9FN_4O_{10}$: C, 22.79; H, 2.87; F, 6.01; N, 17.22. Found: C, 22.50; H, 3.01; F, 6.40; N, 17.67.

To those skilled in the art, many modifications and variations of the present invention are possible in light of the above teachings. It is therefore to be understood that the present invention can be practiced otherwise than as specifically described herein and still be within the spirit and scope of the appended claims.

What is claimed and desired to be secured by Letters Patent of the United States is:

1. 2,2-dinitropropyl 2-fluoro-2,2-dinitroethyl formal.
2. A method of preparing 2,2-dinitropropyl 2-fluoro-2,2-dinitroethyl formal by the following steps in order:
   (1) reacting one mole of formaldehyde with each mole of 2,2-dinitropropanol in the presence of an excess of aluminum chloride to produce chloromethyl 2,2-dinitropropyl ether;
   (2) isolating the product chloromethyl 2,2-dinitropropyl ether;
   (3) reacting one mole of 2-fluoro-2,2-dinitroethanol with each mole of chloromethyl 2,2-dinitropropyl ether in the presence of titanium tetrachloride to produce 2,2-dinitropropyl 2-fluoro-2,2-dinitroethyl formal; and
   (4) isolating the product 2,2-dinitropropyl 2-fluoro-2,2-dinitroethyl formal.
3. The process of claim 2 wherein steps (1) and (3) are performed in an atmosphere of a dry inert gas.
4. The process of claim 3 wherein the reaction temperature in step (1) is from −5° C. to 5° C.
5. The process of claim 3 wherein the reaction temperature in step (3) is from 50° C. to 90° C.
6. The process of claim 3 wherein a catalytic amount of titanium tetrachloride is used in step (3).

* * * * *